United States Patent [19]
Miller

[11] Patent Number: 5,998,679
[45] Date of Patent: Dec. 7, 1999

[54] METHODS FOR CONVERTING LOWER ALKANES AND ALKANES TO ALCOHOLS AND DIOLS

[75] Inventor: Jorge Miller, Houston, Tex.

[73] Assignee: JLM Technology, Ltd., Houston, Tex.

[21] Appl. No.: 09/121,768

[22] Filed: Jul. 26, 1998

Related U.S. Application Data

[60] Provisional application No. 60/086,089, May 20, 1998.
[51] Int. Cl.$^6$ ............................. C07C 29/62; C07C 29/00
[52] U.S. Cl. ............................................. 568/859; 568/893
[58] Field of Search ...................................... 568/859, 893

[56] References Cited

U.S. PATENT DOCUMENTS

| | | |
|---|---|---|
| 3,172,915 | 3/1965 | Borkowski et al. . |
| 5,243,098 | 9/1993 | Miller et al. ............................. 568/893 |
| 5,334,777 | 8/1994 | Miller et al. ............................. 568/859 |

*Primary Examiner*—Michael G. Ambrose
*Attorney, Agent, or Firm*—Browning Bushman

[57] ABSTRACT

The present invention is directed to methods for converting lower alkanes and alkenes to the corresponding lower alkanols and diols. In the methods of the present invention, a gaseous halogen, preferably bromine, is produced by decomposing a metal halide in a liquid having a melting point below and a boiling point above the decomposition temperature of the metal halide. The preferred liquid is molten, hydrated ferric chloride maintained at a temperature between about 37–280° C. The lower alkane or alkene is halogenated in a gas phase reaction with the produced halogen. The alkyl halide or alkyl dihalide is contacted with a metal hydroxide, preferably an aqueous solution of ferric hydroxide, to regenerate the metal halide and produce the corresponding lower alkanol or diol. The present invention is particularly efficient for converting methane to methanol using ferric bromide to provide the halogen.

25 Claims, 1 Drawing Sheet

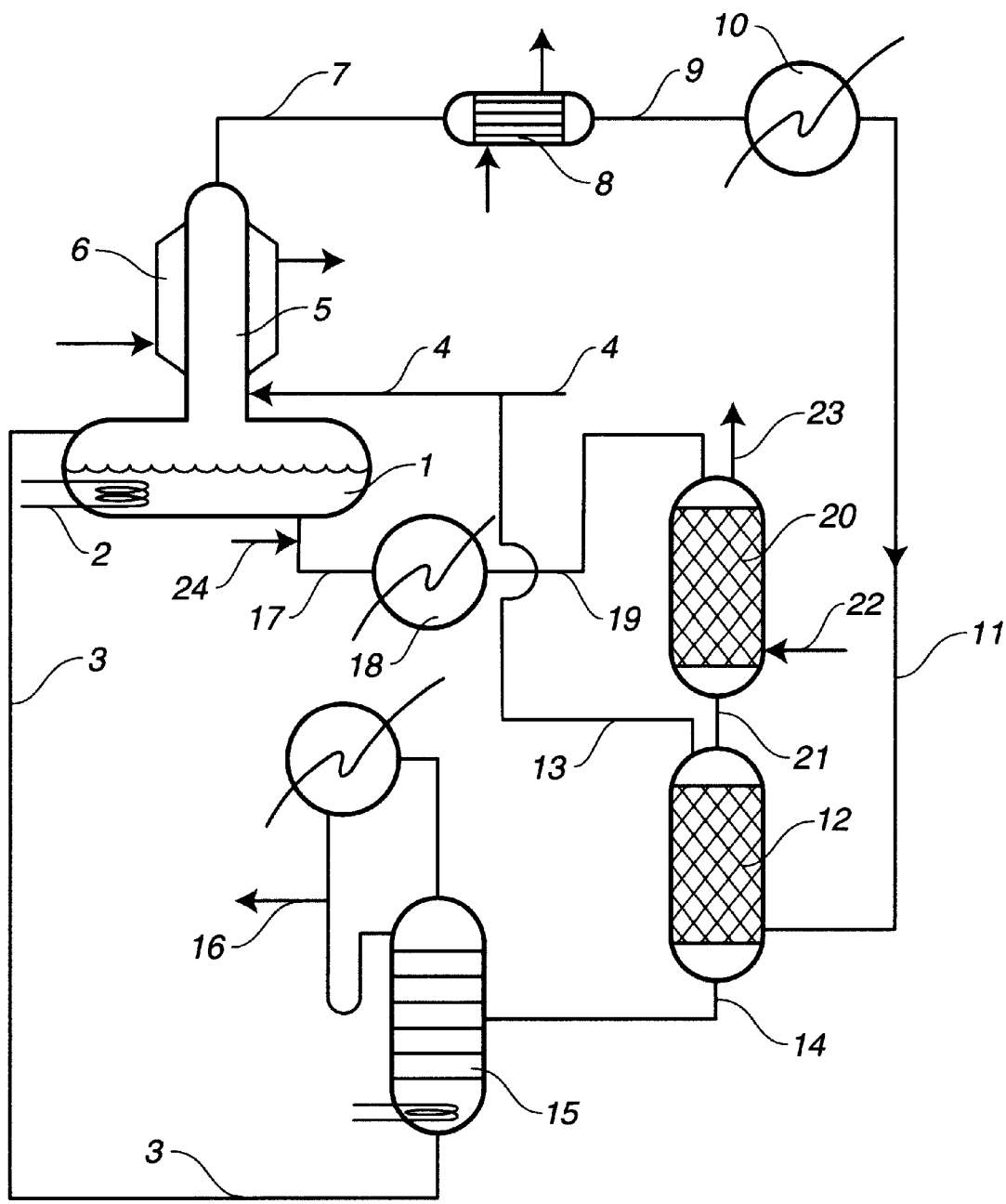

METHODS FOR CONVERTING LOWER ALKANES AND ALKANES TO ALCOHOLS AND DIOLS

This application claims the benefit of U.S. Provisional Application Ser. No. 60/086,089, filed May 20, 1998.

BACKGROUND OF THE INVENTION

I. Field of the Invention

The present invention generally relates to methods for converting alkanes and alkenes to, respectively, alcohols and diols. More specifically, the present invention is directed to conversion methods using liquid and gas phase reactions with liquid reactants which are regenerated and recycled in the process.

II. Description of the Background

Methane has previously been converted to methanol by the halogenation of methane followed by hydrolysis of the methyl halide to form the alcohol. For example, gaseous chlorine has been used to chlorinate methane to form chlorinated methanes, principally methyl chloride, together with other chlorides, i.e., dichloromethane, trichloromethane and carbon tetrachloride. Alternatively, methane has been subjected to oxychlorination with oxygen and hydrochloric acid to form those compounds. The chlorinated methanes produced are hydrolyzed in the vapor phase to produce methanol, formaldehyde, formic acid and by-products, including carbon dioxide and hydrochloric acid, depending on the chlorination selectivity. Hydrochloric acid is produced or used in the halogenation of methane by either method and must be recovered, dehydrated by azeotropic distillation and recycled. Corrosion and problems involved with the handling of chlorine and hydrochloric acid are substantial. Many have tried to solve these problems.

U.S. Pat. No. 3,172,915 to Borkowski, et al. proposed a process for converting methane to methanol. Borkowski disclosed the chlorination of methane using ferric chloride at high temperatures to produce chloromethanes and hydrogen chlorides. This chlorination required temperatures in the range of 220–800° C., more preferably 250–450° C., and long residence times, e.g., more than one hour. Further, this process was hindered by the production of a mixture of chlorination products, e.g., chloromethane, dichloromethane, trichloromethane and carbon tetrachloride, which must be separated before hydrolysis to produce methanol. Other disadvantages result from the energy required to dry the ferric chloride and from the corrosion and handling problems inherent with hydrochloric acid.

U.S. Pat. No. 5,243,098 to Miller disclosed another method for converting methane to methanol. Miller disclosed the reaction of methane with cupric chloride to produce chloromethane and hydrochloric acid. These intermediates were then reacted with steam and a catalyst containing magnesium oxide to produce methanol and magnesium chloride. Magnesium oxide was regenerated by contacting the magnesium chloride by-product with air and oxygen. Cupric chloride was regenerated by contacting the cuprous chloride by-product with air and hydrochloric acid. While these reactions proceed at favorable rates, attrition of the solid reactants, i.e., cupric and magnesium oxide, was significant. Special filters and processes were required to recover and regenerate these reactants in the required particle size. Miller also suggested the use of cupric bromide and magnesium zeolite as alternative reactants. Because of the attrition of the reactants, difficulties associated with the handling of solids and the special filters and processes required to regenerate the reactants, this process has proved unsatisfactory. U.S. Pat. No. 5,334,777, also to Miller, disclosed a substantially identical process for converting ethene to ethylene glycol.

While the foregoing processes have disclosed methods for converting alkanes and alkenes to, respectively, alkanols and diols, those skilled in the art have continued to search for commercially viable processes, particularly commercially viable processes for converting methane to methanol. Such processes are particularly desired by the oil and gas industry in order to reduce the high costs of handling, transporting and storing natural gas. These costs can be reduced significantly if the gas, principally methane and ethane, is converted to methanol and ethanol. Economical and efficient processes for such conversion would find wide use in remote gas fields, e.g., in the North Slope of Alaska, in the North Sea and at other offshore locations.

Thus, there has been a long felt but unfulfilled need for more economical and more efficient methods for converting methane and other lower hydrocarbons to, respectively, methanol and corresponding alkanols and diols. The present invention solves those needs by providing methods with faster reaction kinetics, lower operating temperatures, fluid (liquid and gas) reactants which are easily pumped through the process equipment, efficient regeneration of reactants and little or no attrition of reactant by using liquids which can be readily pumped and recovered.

SUMMARY OF THE INVENTION

The present invention is directed to methods for producing lower alkanols and diols from corresponding lower alkanes and alkenes, respectively. Most preferably, the methods are useful for converting methane to methanol.

In the methods of the present invention, a gaseous halogen is produced by decomposing a metal halide in a liquid having a melting point below and a boiling point above the decomposition temperature of the metal halide. The preferred gaseous halogen is bromine. Most preferably the bromine is produced by the decomposition of ferric bromide, at a temperatures above about 120° C. Exemplary salts which can be used to provide this molten liquid include the hydrated chlorides of iron, nickel, manganese, zinc, calcium and antimony. Most preferred is hydrated ferric chloride which is a liquid in the temperature range of about 37–280° C.

The halogen gas, preferably bromine, so produced is reacted with a lower alkane or alkene, preferably the hydrocarbon gases having up to five carbon atoms, in the gas phase. These reactions typically proceed rapidly at temperatures above about 250° C. for bromination of the alkanes. Reaction with an alkane produces alkyl halide and hydrogen halide gases which are reacted with a metal hydroxide, most preferably ferric hydroxide, to regenerate the metal halide and to produce the lower alkanol corresponding to the alkane. Preferably this reaction proceeds in the liquid phase as these gases are passed through an aqueous solution of the metal hydroxide.

In the most preferred embodiments, the metal halide, preferably a metallic halide and most preferably ferric bromide, decomposes to produce a metal halide of a lower oxidation state, preferably a metallous halide and most preferably ferrous bromide, in addition to the halogen gas. In the most preferred methods, the reaction liquid including this metallous halide is pumped from the reaction chamber, mixed with additional water to prevent crystallization and oxidized to regenerate the metallic halide and to produce the aqueous solution of metal hydroxide.

A substantially identical method produces lower diols from the corresponding lower alkenes. The process step described above is employed to produce the gaseous halogen, preferably bromine, for reaction with the lower alkene. In a gas phase reaction, the halogen, preferably bromine, adds across the double bond of the alkene to produce the corresponding alkyl dihalide. This addition proceeds rapidly at mild temperatures, as low as 40° C. for the bromination of ethylene. The dihalide produced is reacted with the metal hydroxide in accord with the process described above to regenerate the metal halide and produce the corresponding lower diol.

The liquids and gases used as reactants and produced as intermediates by the methods of the present invention are economically and efficiently moved between the reactors greatly reducing the costs associated with prior methods which required solids transport systems. Further, because the processes of the present invention proceed rapidly at relatively low temperatures with the exception of the gas phase reaction of halogen and hydrocarbon, the costs of constructing and operating a methanol conversion plant using the methods of the present invention will be significantly reduced.

Thus, the long felt, but unfulfilled need for improved methods for converting lower alkanes and alkenes to corresponding alkanols and diols, most significantly for converting methane to methanol, have been met. These and other meritorious features and advantages of the present invention will be more fully appreciated from the following description and claims.

BRIEF DESCRIPTION OF THE DRAWINGS

Other features and intended advantages of the present invention will be more readily apparent by the references to the following detailed description in connection with the accompanying drawing wherein:

The FIGURE is a flow diagram illustrating a process for producing lower alkanols and diols in accord with the present invention.

While the invention will be described in connection with the presently preferred embodiments, it will be understood that it is not intended to limit the invention to those embodiments. On the contrary, it is intended to cover all alternatives, modifications and equivalents as may be included in the spirit of the invention as defined in the appended claims.

DETAILED DESCRIPTION OF THE PREFERRED EMBODIMENTS

The present invention provides improved, more efficient and more economical methods for converting methane to methanol and more generally for converting lower alkanes and alkenes to the corresponding alkanols and diols. The invention provides a direct conversion through liquid phase and gas phase reactions. By employing only liquids and gases, the costs of transporting reactants and products between reactors in the conversion system are greatly reduced. Further, reactants are regenerated and recycled in the process. Finally, attrition of reactants has been substantially eliminated.

In its broadest sense, the methods of the present invention comprise three steps: the liquid phase decomposition of a metal halide to produce a gaseous halogen; a gas phase reaction of the halogen with a lower alkane or alkene to produce, respectively, the corresponding alkyl halide or alkyl dihalide; and the liquid phase reaction of the alkyl halide or alkyl dihalide with a metal hydroxide to produce the corresponding lower alkanol or diol.

In its most preferred embodiment, gaseous bromine is produced by the decomposition of ferric bromide from molten, hydrated ferric chloride maintained at a temperature of about 110–280° C. The resulting bromine gas is reacted in the gas phase with an alkane or alkene, most preferably methane at a temperature greater than about 250° C., to produce, respectively, an alkyl halide or alkyl dihalide, most preferably methyl bromide. The resulting alkyl halide or dihalide, preferably methyl bromide, is passed through an aqueous solution of metal hydroxide, preferably ferric hydroxide, where it is hydrolyzed to the corresponding alkanol or diol, preferably methanol. The produced alkanol or diol is readily separated and recovered by conventional means.

In a further advantage offered by the methods of the present invention, by-products produced in the foregoing process, e.g., ferrous bromide and hydrogen bromide, are readily converted to the required reactants, thus eliminating attrition of those materials.

The methods of the present invention will be more readily apparent from the following brief description of the chemical reactions using the most preferred embodiment, i.e., the conversion of methane to methanol using ferric bromide.

A mixture of ferric bromide and hydrated ferric chloride is prepared in a first reactor. The ferric bromide decomposes at a temperature of above about 120° C. to yield ferrous bromide and bromine gas. Hydrated ferric chloride melts at a temperature of about 37° C. and remains liquid through its boiling point at about 280° C. Accordingly, upon the addition of heat the reactor will contain a metal halide (ferric bromide) in a liquid (hydrated ferric chloride) having a melting point below and a boiling point above the decomposition temperature of the metal halide. Addition of heat results in the generation of bromine according to reaction (1).

$$2FeBr_3 \xrightarrow{\Delta} 2FeBr_2 + Br_2 \qquad (1)$$

At temperatures above about 120° C., gaseous bromine will be generated by the decomposition of reaction 1.

The combination of ferric bromide and hydrated ferric chloride is particularly advantageous for the reactions of the present invention. The use of bromine to halogenate the lower hydrocarbon gases reduces the instances of multiple chlorination. Hydrated ferric chloride remains liquid from about 37–280° C. Ferric chloride hexahydrate melts at 37° C. By evaporating about half of the water of hydration the liquid boils at about 134° C. If the water vapor is condensed and continuously returned, the temperature of the molten liquid remains constant. Thus, by controlling the water content, it is possible to have a constant boiling temperature from about 112° C. to about 280° C. Accordingly, hydrated ferric chloride provides a liquid offering a wide range of operating temperatures. Further, while ferric bromide, added to this ferric chloride liquid, will decompose to produce bromine gas in this temperature range, at these relatively low temperatures, ferric chloride does not decompose to produce chlorine gas. Finally, any chlorine gas which might be produced would quickly be decomposed by reaction with water at these temperatures.

The bromine gas is removed from the reactor and mixed with a gaseous lower hydrocarbon, preferably methane. The gaseous mixture readily reacts to produce the corresponding chlorinated hydrocarbon, preferably methyl chloride. The reaction proceeds rapidly at temperatures above about 250° C. according to reaction (2).

$$CH_4 + Br_2 \xrightarrow{\Delta} CH_3Br + HBr \qquad (2)$$

The methyl bromide produced in this reaction is conveyed to another reactor where it is reacted with a metal hydroxide, preferably ferric hydroxide, most preferably by countercurrent passage through an aqueous hydroxide solution in accord with reaction (3).

$$3CH_3Br + Fe(OH)_3 \rightarrow FeBr_3 + 3CH_3OH \qquad (3)$$

This reaction proceeds rapidly at temperatures from about 40–80° C. In addition to producing methanol or the alkanol or diol corresponding to the initial alkane or alkene, the starting metal halide, preferably ferric bromide, is regenerated and can be recovered for further use.

The halogenation of the alkane according to reaction 2 produces as a by-product a hydrogen halide, preferably hydrogen bromide. That by-product can be used to regenerate the initial metal halide, preferably ferric bromide, according to reaction (4).

$$3HBr + Fe(OH)_3 \rightarrow FeBr_3 + 3H_2O \qquad (4)$$

Thus, the gases generated in the halogenation reaction 2 are all passed through the aqueous hydroxide solution to produce the desired alcohol and to regenerate the metal halide.

Finally, ferrous bromide produced in the first reactor from the decomposition of ferric bromide is readily converted to ferric bromide and ferric hydroxide according to reaction (5).

$$12FeBr_2 + 3O_2 + 6H_2O \rightarrow 8FeBr_3 + 4Fe(OH)_3 \qquad (5)$$

This reaction proceeds rapidly at temperatures of about 40–60° C. Liquid containing ferrous bromide withdrawn from the first reactor must be diluted with water to prevent crystallization at the lower reaction temperatures. Counter-current passage of air or oxygen through the resulting aqueous solution oxidizes and hydrolyzes the ferrous bromide according to reaction 5.

In the halogenation of alkenes, the halogen, preferably bromine, simply adds across the double bond according to the reaction of (6).

$$C_2H_4 + Br_2 \xrightarrow{\Delta} C_2H_4Br_2 \qquad (6)$$

Thus, no by-product gases are formed in this reaction. This reaction proceeds in the gas phase at lower temperatures, e.g., temperatures from about 40–60° C., than those required for the halogenation of alkanes.

The resulting alkyl dihalide is passed through a ferric hydroxide solution as described above to produce the corresponding diol and to regenerate ferric bromide in accord with reaction (7).

$$3C_2H_4Br_2 + 2Fe(OH)_3 \rightarrow 3C_2H_4(OH)_2 + 2FeBr_3 \qquad (7)$$

Thus, ferric bromide is regenerated and recycled in this process.

The methods of the present invention will now be described in connection with the flow diagram of the FIGURE. A mixture of hydrated ferric chloride, ferric bromide and, optionally, water, is fed through line 3 to reactor 1. The mixture should include at least 5 percent-by-weight ferric bromide. Heater 2 warms the liquid to the decomposition temperature of ferric bromide, preferably to a temperature from about 112–280° C., most preferably to about 134° C. At this temperature, bromine is produced as a gas according to reaction (1). Condenser 5 surrounded by water cooling jacket 6 is located at the top of reactor 1 in order to condense excess water and bromine back into the reactor. Gases escaping reactor 1, including bromine and evaporated water are mixed with methane from line 4 before passing through condenser 5.

Cooled methane and bromine in a ratio defined by their outlet vapor pressures pass through line 7 to oil heater 8 where they are reacted, preferably at temperatures above about 250° C. to form methyl bromide and hydrogen bromide according to reaction (2). The reaction products are passed through line 9 to cooler 10 where their temperature is reduced. However, cooling should not be sufficient to result in condensation.

The cooled gases containing methyl bromide and hydrogen bromide are directed through line 11 to the lower side of absorber 12 where they pass upwardly through a countercurrent flow of liquid comprising an aqueous ferric hydroxide solution. In absorber 12, these gases react with the ferric hydroxide according to reactions (3) and (4) to produce methanol and ferric bromide.

Gases containing unreacted methane and water vapor from which the methyl bromide and hydrogen bromide have been stripped are returned to input line 4 through line 13. Liquid is withdrawn from the bottom of absorber 12 through line 14 for transport to distillation column 15 where methyl alcohol and water are vaccum stripped from the liquid and recovered through line 16. When used in a system to convert alkenes to diols, the diols should be stripped by vacuum steam distillation. Solution containing regenerated ferric bromide is withdrawn from the bottom of column 15 for return to input line 3.

Liquid containing spent ferrous bromide is withdrawn from reactor 1 through line 17 and directed to cooler 18. Sufficient water must be added through line 24 to prevent crystallization as the molten liquid is cooled. The cooled solution is transported by line 19 to aerator 20. Air injected through line 22 oxidizes the ferrous bromide in aqueous solution to ferric bromide and ferric hydroxide according to reaction (5). The resulting aqueous solution of ferric hydroxide and ferric bromide is conveyed to absorber 12 through line 21. Excess air exits aerator 20 through line 23.

Thus, the FIGURE illustrates a convenient system for converting a lower alkane or alkene to its corresponding alkanol or diol.

The foregoing description has been directed in primary part to a particular preferred embodiment in accord with the requirements of the Patent Statutes and for purposes of explanation and illustration. It will be apparent, however, to those skilled in the art that many modifications and changes in the specifically described methods may be made without departing from the true scope and spirit of the invention. For example, while the invention has been illustrated using the preferred reactants, e.g., ferric bromide, hydrated ferric chloride and ferric hydroxide, other metal compounds having the desired physical and chemical properties, described herein may be used. Therefore, the invention is not restricted to the preferred embodiment described and illustrated but covers all modifications which may fall within the scope of the following claims.

What is claimed is:

1. A method for converting methane to methanol, comprising:

decomposing ferric bromide from a molten mixture of ferric bromide and hydrated ferric chloride to produce bromine gas and ferrous bromide;

reacting said bromine gas with methane to produce methyl bromide and hydrogen bromide gases; and passing said gases through an aqueous solution of ferric hydroxide to produce methanol and to regenerate said ferric bromide.

2. The method of claim 1 wherein said ferrous bromide is dissolved in water and oxidized to regenerate said ferric bromide and to produce said aqueous solution of ferric hydroxide.

3. The method of claim 2 wherein said molten mixture is maintained at a temperature of about 110–280° C.

4. The method of claim 3 wherein said bromine and methane are reacted at a temperature greater than about 250° C.

5. The method of claim 2 wherein said solution is maintained at a temperature of about 40–80° C.

6. A method for producing a lower alkanol from a corresponding lower alkane, comprising:

producing a gaseous halogen by decomposing a metal halide in a liquid, said liquid having a melting point below and a boiling point above the decomposition temperature of said metal halide;

reacting said halogen with a lower alkane to produce an alkyl halide and hydrogen halide gases; and reacting said gases with a metal hydroxide to regenerate said metal halide and to produce a lower alkanol corresponding to said alkane.

7. The method of claim 6 wherein said halogen is bromine.

8. The method of claim 6 wherein said gases are passed through an aqueous solution of said metal hydroxide.

9. The method of claim 8 wherein said metal halide decomposes to produce a metal halide of a lower oxidation state which is later dissolved in water and oxidized to regenerate said metal halide and to produce said aqueous solution of metal hydroxide.

10. The method of claim 6 wherein said alkane has from 1 to 5 carbon atoms.

11. The method of claim 6 wherein said metal halide is ferric bromide, said liquid is molten, hydrated ferric chloride, and said metal hydroxide is ferric hydroxide.

12. The method of claim 11 wherein said gases are passed through an aqueous solution of ferric hydroxide.

13. The method of claim 12 wherein said solution is maintained at a temperature of about 40–80° C.

14. The method of claim 11 wherein said liquid is maintained at a temperature of about 110–280° C.

15. The method of claim 11 wherein said halogen and lower alkane are reacted at a temperature greater than about 250° C.

16. A method for producing a lower diol from a corresponding alkene, comprising:

producing a gaseous halogen by decomposing a metal halide in a liquid, said liquid having a melting point below and a boiling point above the decomposition temperature of said metal halide;

reacting said halogen with a lower alkene to produce an alkyl dihalide gas; and reacting said gas with a metal hydroxide to regenerate said metal halide and to produce a lower diol corresponding to said alkene.

17. The method of claim 16 wherein said halogen is bromine.

18. The method of claim 16 wherein said alkyl dihalide is passed through an aqueous solution of said metal hydroxide.

19. The method of claim 18 wherein said metal halide decomposes to produce a metal halide of a lower oxidation state which is later dissolved in water and oxidized to regenerate said metal halide and to produce said aqueous solution of metal hydroxide.

20. The method of claim 16 wherein said alkene has from 2 to 5 carbon atoms.

21. The method of claim 22 wherein said metal halide is ferric bromide, said liquid is molten, hydrated ferric chloride, and said metal hydroxide is ferric hydroxide.

22. The method of claim 21 wherein said gas is passed through an aqueous solution of ferric hydroxide.

23. The method of claim 22 wherein said solution is maintained at a temperature of about 40–80° C.

24. The method of claim 21 wherein said liquid is maintained at a temperature of about 110–280° C.

25. The method of claim 21 wherein said halogen and lower alkene are reacted at a temperature greater than about 40° C.

* * * * *